United States Patent [19]

Helsley et al.

[11] Patent Number: 4,812,456

[45] Date of Patent: Mar. 14, 1989

[54] 1-(N-(2-ALKYLTHIO-10H-PHENOTHIAZIN-10-YL)ALKYL)-4-BENZOYLPIPERIDINES AND PHARMACEUTICAL USE

[75] Inventors: Grover C. Helsley, Pluckemin; Larry Davis, Sergeantsville; Gordon E. Olsen, Somerset, all of N.J.

[73] Assignee: Hoechst-Roussel Pharmaceuticals Inc., Somerville, N.J.

[21] Appl. No.: 49,234

[22] Filed: May 13, 1987

[51] Int. Cl.[4] ..................... A61K 31/54; C07D 417/06
[52] U.S. Cl. ..................................... 514/225.5; 544/46
[58] Field of Search ................ 544/46; 514/223, 225.5

[56] References Cited

U.S. PATENT DOCUMENTS

| | | | |
|---|---|---|---|
| 3,063,996 | 11/1962 | Gordon et al. | 544/46 X |
| 3,130,194 | 4/1964 | Jacob et al. | 544/46 |
| 3,305,547 | 2/1967 | Stach et al. | 544/46 |
| 3,445,464 | 5/1969 | Jucker et al. | 544/46 X |
| 4,018,922 | 4/1977 | Derible et al. | 544/46 X |
| 4,021,552 | 5/1977 | Welstead et al. | 514/223 |

OTHER PUBLICATIONS

Burgers Medicinal Chemistry, Fourth Edition, Part III, Chapter 56 (1979) pp. 873–888.
Costall et al, J. Pharm. Pharmac., vol. 30 (1978) pp. 771–778.
Boswell et al, J. Med. Chem., vol. 21 (1978) pp. 136–139.
Johnson et al, Chemical Abstracts, vol. 92 (1980) 208923k.
Jacob et al, Chemical Abstracts, vol. 57 (1962) 4677i.

*Primary Examiner*—Richard L. Raymond
*Attorney, Agent, or Firm*—R. Wittekind

[57] ABSTRACT

This invention relates to 1-[n-(2-alkylthio-10H-phenothiazin-10-yl)alkyl]-4-benzoylpiperidines and methods for treating pain or psychosis utilizing compounds or compositions thereof.

7 Claims, No Drawings

1-(N-(2-ALKYLTHIO-10H-PHENOTHIAZIN-10-YL)ALKYL)-4-BENZOYLPIPERIDINES AND PHARMACEUTICAL USE

This invention relates to 1-[n-(2-alkylthio-10H-phenothiazin-10-yl)alkyl]-4-benzoylpiperidines. More particularly, this invention relates to 1-[n-(2-alkylthio-10H-phenothiazin-10-yl)alkyl]-4-benzoylpiperidines of the formula:

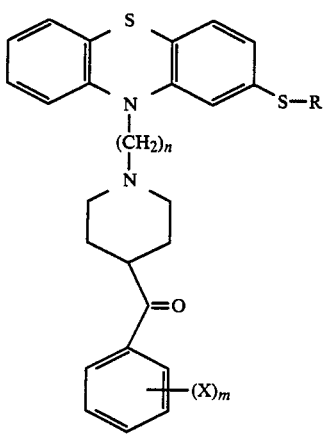

wherein R is an alkyl radical having up to 6 carbon atoms (e.g. methyl, ethyl, and 2-propyl, 1-butyl, 1-pentyl, 3-hexyl and the like); n is an integer having a value from 2 to 4 inclusive; m is an integer having a value from 0 to 2 inclusive, and X is a radical selected from the group consisting of fluorine, chlorine, bromine, iodine, and trifluoromethyl; the geometrical isomers, optical antipodes, or pharmaceutically acceptable acid addition salts thereof. For purposes of this invention, R is preferably an alkyl radical having up to 3 carbon atoms, most preferably methyl, and X is preferably fluorine or chlorine.

Subgeneric to the compounds of the invention are compounds of the formula:

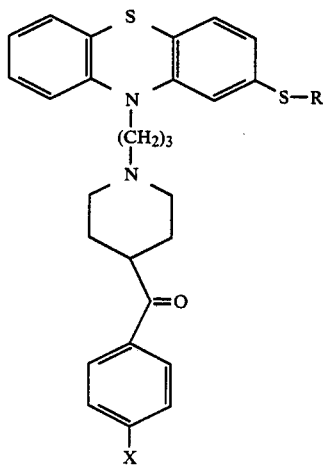

Formula II wherein R and X are as previously described.

The 1-[n-(2-alkylthio-10H-phenothiazin-10-yl)alkyl]-4-benzoylpiperidines of this invention are prepared by reacting a 4-benzoylpiperidine of the formula:

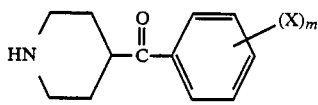

wherein X and m are as previously described, with a 10-(haloalkyl)-2-alkylthiophenothiazine of the formula:

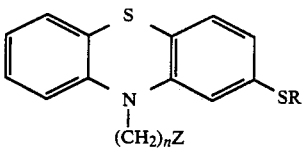

wherein n and R are as previously described and Z is chlorine, bromine or iodine, preferably chlorine. The reaction is conducted in a suitable inert organic solvent, in the presence of an acid acceptor, at a temperature of from about 70° C. 130° C., preferably from about 70° C. to about 90° C. Suitable solvents for this reaction include aromatic hydrocarbons such as, for example, benzene, xylene, toluene, and the like; polar as well as aprotic solvents such as, for example, dimethylformamide, dimethylacetamide, dimethylsulfoxide, hexamethylphosphoramide, and the like; dimethylformamide is preferred. As acid acceptors there may be mentioned inorganic bases including alkali metal hydroxides, carbonates and bicarbonates such as, for example, potassium hydroxide, sodium hydroxide, potassium carbonate, sodium carbonate, potassium bicarbonate and sodium bicarbonate. Sodium bicarbonate is preferred. Desirably, the reaction is conducted under anhydrous conditions.

The 4-benzoylpiperidines employed as starting materials in the production of the compounds of the invention are prepared by any of several well known processes. See, for example, R. L. Duncan, Jr., et al., *J. Med. Chem.*, 13 (1), 1 (1970) (hereinafter "Duncan et al.") and R. F. Boswell, Jr., et al., *J. Med. Chem.*, 21 (1), 136 (1978) (hereinafter "Boswell et al."). As described by Duncan et al., the treatment of N-acetylisonipecotic acid with thionyl chloride forms an acid chloride which can be reacted with a desired benzene derivative (e.g. fluorobenzene) and hydrolyzed to a phenyl-substituted 4-benzoylpiperidine as previously described. Similarly, the hydrolysis of the reaction product of N-acetylisonipecotic acid chloride and a halo-substituted benzene derivative as a means of synthesizing phenyl substituted 4-benzoylpiperidines is disclosed by Boswell et al. Duncan et al. further disclose the dehydration of 1-acetylisonipecotamide followed by the reaction of the resulting nitrile with phenyl magnesium halide and the subsequent hydrolysis of the Grignard derived intermediate as an alternative means of synthesizing certain phenyl-substituted 4-benzoylpiperidines (e.g. 4-(m-trifluoromethyl)benzoyl-piperidines.

The resultant compounds are isolated by conventional techniques such as for example, distillation, chromatography, crystallization or by conversion to a pharmaceutically acceptable acid addition salt.

Included among the compounds of this invention are: 4-(benzoyl)-1-[4-(2-methylthio-10H-phenothiazin-10-yl)butyl]-piperdine;
(4-chlorobenzoyl)-1-[3-(2-methylthio-10H-phenothiazin-10-yl)-propyl]piperdine;

4-(benzoyl)-1-[3-(2-methylthio-10H-phenothiazin-10-yl)propyl]piperidine;

4-(3-fluorobenzoyl)-1-[3-(2-methylthio-10H-phenothiazin-10-yl)-propyl]piperidine;

4-(2-fluorobenzoyl)-1-[3-(2-methylthio-10H-phenothiazin-10-yl)-propyl]piperidine;

1-[3-(2-methylthio-10H-phenothiazin-10-yl)propyl]-4-(4-(trifluoromethyl) benzoyl]piperdine;

4-(3,5-difluorobenzoyl)-1-[3-(2-methylthio-10H-phenothiazin-10-yl) propyl]piperdine;

4-(4-chlorobenzoyl)-1-[2-(2-methylthio-10H-phenothiazin-10-yl)ethyl]piperidine;

4-(2,4-dichlorobenzoyl)-1-[2-(2-methylthio-10H-phenothiazin-10-yl) ethyl]piperidine;

1-[2-(2-ethylthio-10H-phenothiazin-10-yl)ethyl]-4-[4-(trifluoromethyl) benzoyl]piperidine; and 4-(4-bromobenzoyl)-1-[3-(2-isopropylthio-10H-phenothiazin-10-yl) propyl]piperdine.

The 1-[n-(2-alkylthio-10H-phenothiazin-10-yl)alkyl]-4-benzoylpiperdines of this invention are useful as analgetics as a result of their ability to alleviate pain in mammals.

The procedure employed to determine analgesic utility is a modification of the phenyl-p-quinone writhing assay in mice, a standard assay for analgesia (Proc. Soc. Exptl. Bio. Med., 95 729 (1957)]. In the modified procedure phenyl-p-benzoquinone (Eastman, 12.5 mg) is dissolved in 5 ml of 95% ethanol and the solution is diluted to a total volume of 100 ml with distilled water. The solution is administered to the subject mice subcutaneously at a dose of 10 ml per kg of body weight. A characteristic "writh", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously at 15, 30, 45 and 60 minutes prior to administration of the phenyl-p-quinone. Four control groups of 2 animals (8 animals) receive an equal volume of the vehicle. After the administration of the phenyl-p-quinone, the mice are placed separately in one liter beakers, and after five minutes, are observed for ten minutes. The number of writhes for each animal is recorded. The following formula is used to compute the percent inhibition:

$$\frac{\bar{x} \text{ Writhes in Control Group} - \bar{x} \text{ Writhes in Drug Group}}{\bar{x} \text{ Writhes in Control Group}} \times 100$$

The time period with the greatest percent of inhibition is considered the peak time. A dose range determination is generally reserved for those compounds which inhibit writhing by greater than 65-70% at the screening dose.

A dose range determination is run in the same manner as the time response except 10 animals per group are tested at the peak time of test drug activity. Fifty animals, 4 test drug groups, and a vehicle control are employed. Animals are dosed and tested in a randomized manner. A calculated $ED_{50}$, i.e., the estimated dose at which 50% inhibition of writhing is produced, is determined by a computer linear regression analysis. The calculated subcutaneous (s.c.) dose effecting an approximately 50% inhibition of writhing ($ED_{50}$) in mice produced in this assay is as follows:

| Compound | Analgesic Activity (% Inhibition of Writhing) $ED_{50}$ (mg/kg, s.c.) |
|---|---|
| 1-[3-(2-methylthio-10H—phenothiazin-10-yl)propyl]-4-(4-fluorobenzoyl) piperidine fumarate | 6.1 |
| Pentazocine (standard) | 1.3 |

Analgesia production is achieved when the 1-[n-(2-alkylthio-10H-phenothiazin-10-yl)alkyl]-4-benzoylpiperidines of this invention are administered to a subject requiring such treatment as an effective oral, parenteral or intravenous dose of from 0.1 to 50 mg/kg of body weight per day. 1-[n-(2-alkylthio-10H-phenothiazin-10-yl)alkyl]-4-benzoylpiperidines which achieve effective analgesia production at doses of about 5 mg/kg of body weight per day are particularly desirable. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

As a result of their ability to elicit an anti-psychotic response in mammals, the 1-[n-(2-alkylthio-10H-phenothiazin-10yl)alkyl]-4-benzoylpiperidines of this invention have utility as anti-psychotics.

Antipsychotic activity is determined in the climbing mice assay by methods similar to those described by P. Protais, et al., Psychopharmacol, 50, 1 (1976) and B. Costall, Eur. J. Pharmacol., 50, 39 (1978).

The subject CK-1 male mice (23-27 grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally (i.p.) 30 minutes prior to the apomorphine challenge at a screening dose of 10 mg/kg.

For evaluation of climbing, 3 readings are taken at 10, 20 and 30 minutes after apomorphine administration according to the following scale.

| Climbing Behavior Mice with: | Score |
|---|---|
| 4 paws on bottom (no climbing) | 0 |
| 2 paws on the wall (rearing) | 1 |
| 4 paws on the wall (full climb) | 2 |

Mice consistently climbing before the injection of apomorphine are discarded.

With full-developed apomorphine climbing, the animals are hanging onto the cage walls, rather motionless, over longer periods of time. By contrast, climbs due to mere motor stimulation usually last only a few seconds.

The climbing scores are individually totaled (maximum score: 6 per mouse over 3 readings) and the total score for the control group (vehicle intraperitioneally-apomorphine subcutaneously) is set to 100% as per this assay, $ED_{50}$ values with 95% confidence limits, calculated by linear regression analysis are as follows:

| Compound | Anti-Psychotic Activity ($ED_{50}$ mg/kg, i.p.) |
| --- | --- |
| 1-[3-(2-methylthio-10H—phenothiazin-10-yl)propyl]-4-(4-fluorobenzoyl)piperidine fumarate | 1.4 |
| Thioridazine (standard) | 4.1 |

Dosage levels at which the 1-[n-(2-alkylthio-10H-phenothiazin-10-yl)alkyl]-4-benzoylpiperidines of this invention achieve an anti-psychotic response is subject to variation depending upon the particular compound employed. In general, an anti-psychotic response may be elicited at effective doses ranging from about 0.1 to about 50 mg/kg of body weight per day. It is to be understood, however, that for any particular subject, specific dosage regimens should be adjusted according to the individual need and the professional judgement of the person administering or supervising the administration of the aforesaid compound. It is to be further understood that the dosages set forth herein are exemplary only and they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The 1-[n-(2-alkylthio-10H-phenothiazin-10-yl)alkyl]-4-benzoylpiperidines of this invention, while effective themselves, may be formulated and administered in the form of their pharmaceutically acceptable addition salts for purposes of stablity, convenience or crystallization, increased solubiilty and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; and excipient such as starch or lactose, a disintegrating agent such as alginic acid, Promogel ™, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the preceeding type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and nontoxic in the amounts used.

For the purposes of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzylalcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are for illustrative purposes only and are not to be construed as limiting the invention. All temperatures are given in degrees centigrade (°C). Yields are calculated on a molar basis.

EXAMPLE 1

4-(4-Fluorobenzoyl)-1-[3-(2-methylthio-10H-phenothiazin-10-yl)propyl]piperidine fumarate To a stirred solution of sodium bicarbonate (10 g) in 40 ml of dimethylformamide was added 2.5 g of 4-(4-fluorobenzoyl)piperidine in 40 ml of dimethylformamide, and 4.5 g of 10-(3-chloropropyl)-2-methylthiophenothiazine in 20 ml of dimethylformamide. The reaction mixture was stirred at 78° C. for four hours, cooled, and filtered. The filtrate was poured into water and extracted with ethyl acetate. The extract was washed with water, dried over anhydrous magnesium sulfate, filtred and concentrated to an oil. The oil was purified by high pressure liquid chromatography on a silica gel column, utilizing ethyl acetate as the eluent. Concentration of the appropriate fractions yielded 2.97 g (36%) of 4-(4-fluorobenzoyl)-1-[3-(2-methylthio-10H-phenothiazin-10-yl)propyl]piperidine as an oil.

The free base was dissolved in isopropyl alcohol and acidified to a pH of 1 by treatment with fumaric acid (etheral solution) to yield 2.63 g of 4-(4-fluorobenzoyl)-1-[3-(2-methylthio- 10H-phenothiazin-10-yl)propyl]-piperidine fumarate as a solid, mp 192°–194°.

ANALYSIS:

Calculated for $C_{28}H_{29}FN_2OS_2.C_4H_4O_4$: 63.16% C; 5.43% H; 4.61% N

Found: 63.04% C; 5.73% H; 4.47% N

EXAMPLE 2

4-(2,4-Dichlorobenzoyl)-1-[3-(2-methylthio-10H-phenothiazin-10-yl)propyl]piperidine fumarate To 75 ml of dry dimethylformamide was added 2.0 g of 10-(3-chloropropyl)-2-methylthiophenothiazine, 1.7 g of 4-(2,4-dichlorobenzoyl)piperidine, and 5.0 g of sodium bicarbonate. The reaction mixture was stirred at 90° for five hours, poured into 200 ml of water, and extracted with ethyl acetate. This extract was washed with water, dried over anhydrous magnesium sulfate, filtered, and concentrated to an oil. This oil was purified by high pressure liquid chromatography on a silica gel column, utilizing ethyl acetate/dichloromethane (1:2 by volume) as the eluent. Concentration of the appropriate fractions yielded 2.7 g of 4-(2,4-dichlorobenzoyl)-1-[3-(2-methylthio-10H-phenothiazin-10-yl)propyl]piperidine as an oil.

The free base was dissolved in isopropyl alcohol, acidified to a pH of 1 by treatment with a solution of fumaric acid in isopropyl alcohol, and diluted by the addition of diethyl ether. The precipitate was collected and dried to yield 2.1 g (51%) of 4-(2,4-dichlorobenzoyl)-1-[3-(2-methylthio-10H-phenothiazin-10-yl)propyl]piperidine fumarate as a solid, mp @145° C.

ANALYSIS:

Calculated for $C_{28}H_{28}Cl_2N_2OS_2.C_4H_4O_4$: 58.26% C; 4.89% H; 4.25% N

Found: 57.89% C; 5.00% H; 4.20% N

What is claimed is:

1. A compound of the formula

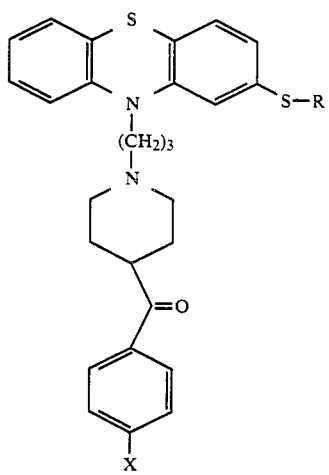

wherein R is an alkyl radical having up to 6 carbon atoms, inclusive; and X is a radical selected from the group consisting of fluorine, chlorine, bromine, iodine, and trifluoromethyl, the geometrical isomers, optical antipodes, or pharmaceutically acceptable acid addition salts thereof.

2. A compound according to claim 1 wherein X is fluorine or chlorine.

3. A compound according to claim 1 wherein R is an alkyl radical having up to 3 carbon atoms, inclusive.

4. The compound od claim 1, which is 4-(4-fluorobenzoyl)-1-[3-(2-methylitho-10H-phenothiazin-10-yl)propyl]piperidine.

5. A pharmaceutical composition comprising a pharmaceutically effective amount of a compound as defined in claim 1 or a pharmaceutically acceptable acid additon salt thereof and a carrier therefor.

6. A method of alleviating pain comprising administering to a mammal in need of pain alleviation, a pain alleviating effective amount, of a compound as defined in claim 1.

7. A method of treating psychosis comprising administering to a mammal in need of psychosis treatment a psychosis treating effective amount of a compound as defined in claim 1.

* * * * *